United States Patent
Harttig

(10) Patent No.: US 8,591,827 B2
(45) Date of Patent: Nov. 26, 2013

(54) STACK OF TEST STRIPS AND METHOD FOR THE PRODUCTION THEREOF

(75) Inventor: Herbert Harttig, Neustadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/418,945

(22) Filed: Mar. 13, 2012

(65) Prior Publication Data

US 2012/0224996 A1  Sep. 6, 2012

Related U.S. Application Data

(63) Continuation of application No. PCT/EP2010/005579, filed on Sep. 11, 2010.

(30) Foreign Application Priority Data

Sep. 24, 2009  (EP) ..................................... 09012125

(51) Int. Cl.
G01N 21/75 (2006.01)
G01N 31/22 (2006.01)
G01N 33/52 (2006.01)
B01L 9/00 (2006.01)

(52) U.S. Cl.
USPC ............................ 422/400; 422/401; 422/563

(58) Field of Classification Search
None
See application file for complete search history.

(56) References Cited

U.S. PATENT DOCUMENTS

| | | | |
|---|---|---|---|
| 4,650,706 A * | 3/1987 | Emmel | 428/40.1 |
| 4,710,351 A * | 12/1987 | Wogoman | 422/50 |
| 5,657,870 A * | 8/1997 | Schottle et al. | 206/459.5 |
| 5,757,666 A | 5/1998 | Schreiber et al. | |
| 5,962,333 A | 10/1999 | Incorvia et al. | |
| 6,319,467 B1 * | 11/2001 | McLernon, III | 600/556 |
| 6,378,701 B1 | 4/2002 | Kuo | |
| 6,378,702 B1 | 4/2002 | Kintzig | |
| 6,514,585 B1 * | 2/2003 | Pearson et al. | 428/40.1 |
| 6,986,923 B1 * | 1/2006 | Junghans et al. | 428/40.1 |
| 7,735,872 B1 * | 6/2010 | Arkwright | 281/45 |
| 2003/0129346 A1 * | 7/2003 | Pearson et al. | 428/40.1 |
| 2003/0185706 A1 * | 10/2003 | Ribi | 422/58 |
| 2004/0161365 A1 * | 8/2004 | Siu Yu | 422/56 |
| 2005/0013731 A1 * | 1/2005 | Burke et al. | 422/56 |
| 2006/0002816 A1 | 1/2006 | Zimmer et al. | |
| 2007/0173740 A1 | 7/2007 | Chan et al. | |

FOREIGN PATENT DOCUMENTS

| | | |
|---|---|---|
| CN | 1227921 A | 9/1999 |
| CN | 1842705 A | 10/2006 |
| DE | 43 13 253 A1 | 10/1994 |
| DE | 10 2005 022 022 A1 | 12/2005 |
| EP | 64691 A1 * | 11/1982 |
| EP | 0 547 709 | 6/1993 |
| EP | 1 329 395 | 7/2003 |
| EP | 2 030 566 | 3/2009 |
| WO | WO 02/08750 | 1/2002 |
| WO | WO 2004/113900 | 12/2004 |
| WO | WO 2007/085438 | 8/2007 |
| WO | WO 2011/035861 | 3/2011 |

* cited by examiner

Primary Examiner — Jill Warden
Assistant Examiner — Brittany Fisher
(74) Attorney, Agent, or Firm — Kreig DeVault LLP

(57) ABSTRACT

A stack of test strips comprises individual test strips which are stacked over each other and carry a test field for examining a bodily fluid sample. Test strips lying one on top of the other are detachably adhesively bonded to each other so that the test strips can be individually removed from the stack, wherein the test fields are packed in chambers and adjacent test strips form the bottom and the lid of such a chamber. A method for producing such a stack of test strips is also disclosed.

19 Claims, 2 Drawing Sheets

STACK OF TEST STRIPS AND METHOD FOR THE PRODUCTION THEREOF

CROSS-REFERENCE TO RELATED APPLICATIONS

The present application is a continuation of International Application No. PCT/EP2010/005579 filed on Sep. 11, 2010, which claims priority to European Patent Application No. 09012125.2 filed on Sep. 24, 2009, each of which is incorporated herein by reference in its entirety.

FIELD OF THE INVENTION

The invention relates to a stack of test strips, comprising individual test strips which are stacked one above the other and carry a test field for examining a body fluid sample.

BACKGROUND

A stack of test strips is known from WO 2007/085438. Test strips together with suitable measuring devices allow a simple and fast determination of an analyte concentration of a body fluid sample, which can also be performed by a medical layperson, for example for measuring the lactate or cholesterol concentration. Also, test strips are in particular used by diabetics who have to examine their blood sugar level several times a day by measuring the glucose concentration of a body fluid sample, usually blood or interstitial fluid.

The test fields of test strips usually are sensitive and therefore have to be protected against harmful environmental influences until use. Therefore, a cost-effective way for this to be accomplished is needed.

SUMMARY

According to one aspect, a stack of test strips is disclosed comprising individual test strips, wherein test strips lying on top of one another are detachably adhesively bonded to each other so that the test strips can be individually removed from the stack. The test fields of the test strips are enclosed in chambers, wherein adjacent test strips form a bottom and a closure of such a chamber. The chambers can also be formed by adhesively bonding the strips so that adjacent strips form the bottom and the ceiling of a chamber therebetween. However, it is also possible that a test strip contains a chamber which has an opening that is closed by an adjacent strip.

In this aspect, each individual test field is protected in a chamber against harmful environmental influences until use. Since said chamber is formed by strips carrying the test fields, moisture-proof packing can be achieved with little effort.

In another aspect, there is disclosed a method for producing such a stack of test strips where individual test strips carrying a test field on their front side are adhesively bonded to form a stack in that in each case the front side of a test strip is adhered to the back side of another test strip. Thereby, the test fields are enclosed in chambers and are sealed therein in a moisture-proof manner. By adhesively bonding the strips, the test fields can be enclosed in chambers in that adjacent strips form the bottom and the closure of a chamber. The closure can form a ceiling of a chamber or may only cover an opening in the chamber ceiling.

For adhesively bonding the individual test strips, an adhesive bead can be circumferentially applied onto each test strip so that the test strips adhere when being placed on top of each other. The effort to apply a separate adhesive bead onto each individual test strip can be avoided in that for adhesively bonding, individual test strips are placed into a holder which holds the individual strips spaced apart from each other in such a manner that the front side of a strip faces the back side of the strip to which it is to be bonded. Subsequently, an adhesive can be filled in the gaps between the strips. The adhesive can be filled in this manner between all strips of a stack at the same time.

For example, the test strip arrangement formed by means of the holder can be dipped with its lateral side into a liquid adhesive so that the adhesive penetrates into the gaps between the individual strips. By the depth with which the test strip arrangement dips into the liquid adhesive, it can be predetermined over which width the test strips are covered on their edges with adhesive. By dipping first one lateral side of the test strip arrangement into the adhesive, the arrangement can be stabilized so that the holder can be removed. Subsequently, the other lateral sides of the test strip arrangement or the stack of test strips can be dipped into the adhesive so that the test fields are circumferentially surrounded by an adhesive.

A stack of test strips necessarily contains always one strip, the front side of which is not covered by a further strip because this test strip forms a front face of the stack. Like the other strips of the stack, this uncovered strip can carry a test field. However, since such a test field would not be protected against harmful environmental influences, it can usually not be used. Therefore, the stack of test strips in one embodiment is covered by a strip without a test field. This means that the last test field of a stack is covered by a strip without a test field.

As explained, the present invention relates to a stack of test strips that includes individual test strips. The term "individual" is used within the context of the present invention in order to distinguish the test strips of a stack of test strips according to the invention from a continuous band that carries a plurality of test fields and is folded into a stack. Individual test strips have a front side, a back side and—in contrast to a continuous band—a circumferential side which connects the front side to the back side. Since test strips are usually made from a film and therefore are typically quite thin, the lateral sides can correspondingly be very narrow and, in the extreme case, may only be an edge. However, in the case of an individual test strip, there is always a circumferential side which usually is a cut surface at which the strip was cut out from a larger film during its manufacture.

BRIEF DESCRIPTION OF THE DRAWINGS

Further details and advantages are set forth by means of an embodiment with reference to the accompanying drawings.

DETAILED DESCRIPTION

Figure 1:
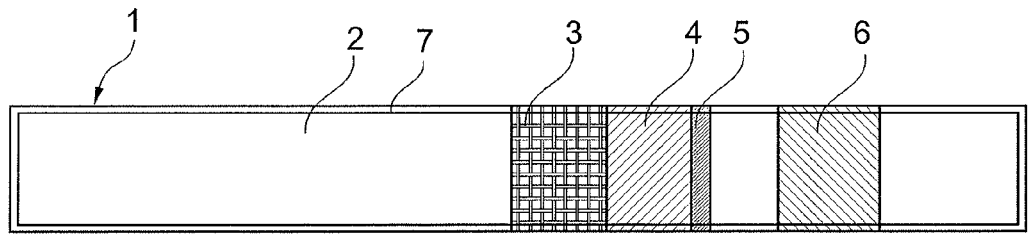
FIG. 1 shows an embodiment of a test strip removed from a stack of test strips.

For purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the illustrated device, and any further applications of the principles of the invention as illustrated therein being contemplated as would normally occur to one skilled in the art to which the invention relates.

Figure 2:
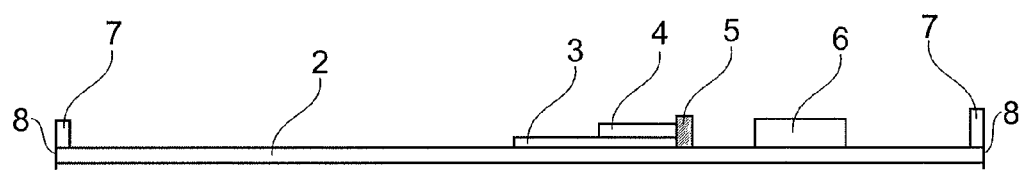
FIG. 2 shows a longitudinal section of FIG. 1.

FIG. 1 illustrates an embodiment of a test strip 1 with a view on its front side, and FIG. 2 illustrates a longitudinal section. Further embodiments of test strips are illustrated in the FIGS. 4 to 8. The test strip 1 includes a strip-shaped carrier material 2, for example a plastic film, and carries on its front side at least one, and in one embodiment exactly one, test field 4 for examining a body fluid sample. The test strip 1 can carry additional auxiliary means for taking samples or examining samples, for example a lancet.

Next to the test field 4, a desiccant 6 can be arranged, for example on the basis of silica gel. The desiccant 6 can be attached as molded part, pill, desiccant bag or film onto the carrier material 2 of the test strip 1. It is also possible to integrate the desiccant 6 in the adhesive 5 by means of which the test field 4 is glued onto the carrier material 2 of the strip.

Figure 3:
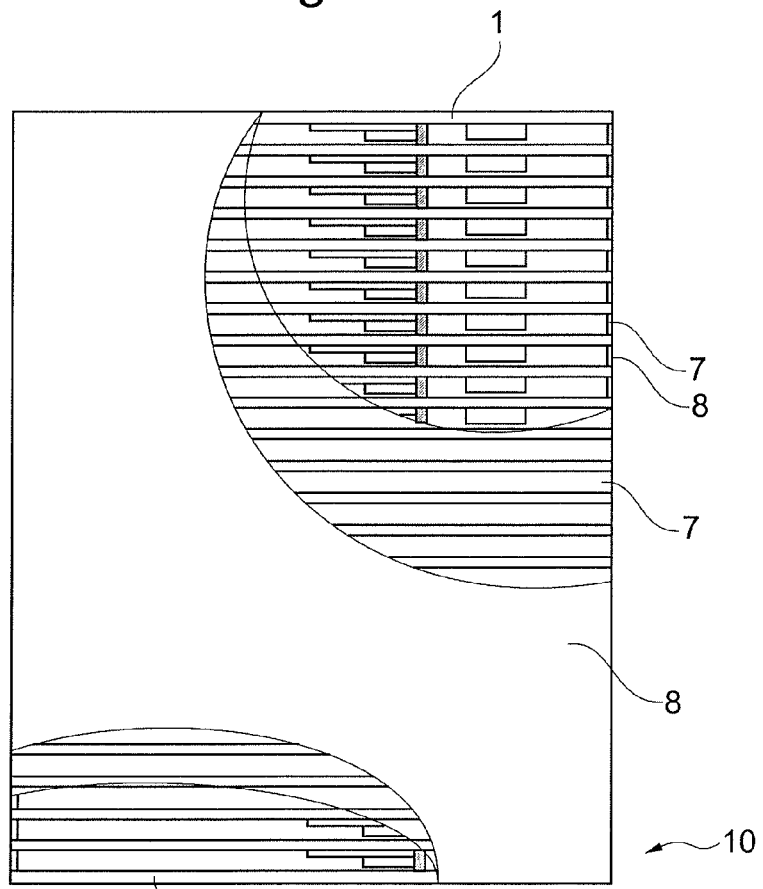
FIG. 3 shows an embodiment of a stack of test strips comprising test strips according to FIG. 1 in a schematic illustration.

The test strip 1 has a circumferential adhesive bead 7 which likewise can contain a desiccant. By means of the circumferential adhesive bead 7, a plurality of individual test strips 1 are glued together to form a stack 10 of test strips which is illustrated as an example in FIG. 3 with a partially cut-open side face.

In the stack 10 of test strips, the test fields 4 of the individual test strips 1 are arranged in chambers which are formed by the adhesive bond of the test strips 1. Adjacent strips 1 form a bottom and a ceiling of a chamber lying between them. The side walls of these chambers are formed by the adhesive 7 which connects adjacent test strips 1. When adhesively bonding the test strips 1, thus, the test fields are enclosed in chambers. A test strip 1 which forms the ceiling of such a chamber forms at the same time also a closure of the chamber.

In one embodiment, the lateral chamber walls have a height measured in the stacking direction that is greater than the height of the test fields 4 measured in the stacking direction. In these chambers, the test fields 4 are packed in a moisture-proof manner until use and are protected against harmful environmental influences.

At its lateral sides, the test strip stack 10 can be surrounded by a protective layer 8 which, for example, can be a film. Particularly suitable are films made of plastic and/or metal, in particular aluminum. The film 8 is preferably glued onto the stack 10, for example with the adhesive 7 by means of which also the individual test strips 1 are glued together. The adhesive 7 bonding the test strips 1 can cover the lateral sides of the stack 10 of test strips and can likewise form a protective layer in this manner. In doing so, the adhesive covers also the lateral sides of the individual strips 1.

A protective layer formed from an adhesive can be used alternatively or additionally to a film 8 covering the side walls of the stack 10. In one particular embodiment, a film 8 which has a low tear strength and thus only insignificantly hinders the removal of a test strip 1 from the stack 10 can be used as a protective layer. Metal films, in particular aluminum films, can in one embodiment be formed very thin and can have a resistance to tear propagation which is lower than its fracture strength. In this manner it can be achieved that during the removal of a test strip 1 from the stack 10, the film 8 breaks along the test strips 1 to be detached from each other.

The test strips 1 are detachably adhesively bonded through the adhesive 7 so that the test strips 1 can be individually removed from the stack 10. Suitable adhesive bonds are common, for example, between adhesive labels and their carrier films or carrier papers from which the adhesive labels can be peeled off. For example, a hot-melt adhesive can also be used as an adhesive 7.

In order to remove an individual test strip 1 from the stack 10, a force can be exerted manually or with a suitable device on an edge of the uppermost test strip 1 so that the test strip 1 disengages from the stack 10 and can be peeled off. In order to facilitate the removal of a test strip 1, the test strips 1 can be stacked offset on top of one another. In that a test strip 1 protrudes laterally or at one of its end beyond the test strip 1 to which it is adhered, the test strip to be removed can be gripped and detached more easily.

In order to prevent that a partial stack with two or more test strips 1 is accidentally detached from the stack 10, the mechanical connection between the test strip 1 to be removed and the remaining stack can be weakened prior to the application of force, for example by grooving.

The adhesive 7 in one embodiment adheres differently on the front side than on the back side of the test strips 1 so that when removing a strip 1 from the stack 10, the adhesive disengages always from the same strip side. A different adhesion of the adhesive 7 can be achieved, for example, by roughening one of the strip sides or in that front and back sides of the strip 1 are made from different materials. In one particular embodiment the adhesive 7 disengages always from the same side of the test strip 1. Through an increased adhesion of the adhesive 7 on the front side of the test strip, adhesively bonding the test fields 7 can advantageously be made easier, for example in that the front side of the strip 1 has a greater roughness than the back side.

The back side of the test strips 1 can be labeled with text or other human or machine readable characters, for example with information on how to remove a test strip 1 from the stack 10, instructions about the use of the test strips, and/or product information. Such information can in particular be printed.

The front side of the last strip of a stack 10 of test strips is not covered by another strip. As already mentioned, the last strip 9 of the stack 10 in one embodiment does not carry a test field 4. This last strip 9 can advantageously serve as a carrier for product information, for example product description, lot number, code number, use-by date and/or production date. The product information can also be printed on the strip. It is also possible, for example, to provide the product information on a separate information carrier, for example a label or an RFID transponder which is adhesively bonded on the strip.

As already mentioned, a plastic film can be used as a carrier material 2 of a test strip 1. Well suited are in particular plastic films having a thickness of 200 to 400 micrometer, for example 300 micrometer. However, thicker or thinner plastic films can also readily be used. The film used is in one embodiment rough on one side. Suitable films can be purchased from the company OfoTec Folien GmbH, Nehren, Germany, under the designation "OFOPROP 10775" or from the company DuPont Teijin Films Luxembourg S.A., Luxembourg, under the designation "Melinex".

By means of an adhesive layer, a strip of a hydrophilized fabric can be fixed on the film. Suitable fabric is distributed, for example, by the company Sefar Holding AG, Thal, Switzerland, under the designation "SEFAR PETEX 07-285/44". For forming a test field, a film strip comprising a detection layer can be glued onto the fabric strip so that a portion of the fabric is uncovered. The film strip is made, for example, from polycarbonate or another plastic. The film strip can have a thickness, for example, of 140 micrometer, wherein greater or smaller thicknesses can also be used. Suitable film strips can be purchased, for example, from the company LOFO High Tech GmbH, Weil am Rhein, Germany, under the designation "Pokalon N 40 GL". The detection layer carried by the film strip contains detection reagents which change color under the influence of glucose. The detection layer contacts the hydrophilized fabric.

The test strips can additionally carry a desiccant, for example a film with bound desiccant, as it is distributed by the company GRACE GmbH & Co. KG, Worms, Germany, under the designation "SP566-10414". In addition, a lancet, for example a piercing element made from a flat-bar steel, can be glued onto the individual test strips. The front side of the test strip can be provided with a recess which divides the front side into two regions. In one of these regions, the test field is glued on, and in the other one, the desiccant or the lancet is glued on.

For covering the last test field 4 of a stack 10 of test strips, a strip 9 from the above-described carrier material of the test strips can be used. This cover strip 9, which in one embodiment does not carry a test field, can be marked with a black dash as a cover.

In order to produce a stack of test strips, the individual test strips and the one cover strip can be sorted and put into a slotted receptacle of a holder. The number of test strips for a stack of test strips is freely selectable. For example, it is possible to connect 10 to 100 test strips, typically 50, to form a stack.

After sorting and putting the strips into the receptacle, the strips 1 are pushed with a lateral side, in one embodiment the longitudinal side, into an adhesive layer. Thereby, the adhesive penetrates into the gaps between the individual strips 1. The adhesive layer into which the stack is pushed can in one embodiment be applied onto a film which subsequently forms the protective layer 8. For example, an aluminum film can be used which, for example, is less than 30 micrometer thick, in particular less than 20 micrometer thick. Particularly suitable is a 16 micrometer thick aluminum film which is coated with a hot-melt adhesive, for example with a hot-melt adhesive distributed by Wacker AG, Munich, Germany, under the designation "Vinnapas B500/VL20". The hot-melt adhesive is applied with a thickness of for example, 100 to 400 micrometer onto the film. In the exemplary embodiment illustrated in FIG. 3, a 200 micrometer thick layer was used.

After the aluminum film has been glued onto one or two side faces of the stack, the holder can be removed so that the aluminum film can also be glued onto the remaining side faces of the stack. The film is in one embodiment dimensioned here such that an overlap is created and the side faces of the stack are completely covered.

Subsequently, a self-adhesive label with product information can be glued onto the cover of the stack formed in this manner.

Possible configurations of the test strips 1 of the stack 10 of test strips are exemplary illustrated in the FIGS. 1 and 2 as well as 4 to 8 and are explained in the following.

The test field 4 can be arranged on an absorbent layer 3, for example on a hydrophilized fabric or fleece, as in the embodiment illustrated in the FIGS. 1 and 2. A body fluid sample can be rapidly absorbed by the absorbent layer and can be brought in contact with detection reagents of the test field 4, in particular if the absorbent layer protrudes underneath the test field 4 and thus allows a particularly simple sampling.

The test field 4, for example, can be provided for a photometric or electrochemical concentration determination. In one embodiment, the test field 4 comprises detection reagents which, upon contact with a body fluid sample, initiate a detection reaction resulting in a change of a physically measurable variable, for example the color or color intensity, for a photometric detection, or in a change of the conductivity or another electrical variable for an electrochemical detection.

For a photometric concentration determination, the test field 4 can comprise a transparent film which carries the detection chemicals. As in the illustrated embodiment, a measurement is performed on the front side of the test strip. However, it is also possible to use a transparent film as a carrier material for the test strip and, accordingly, to perform the photometric measurement on the back side of the test strip 1.

Figure 4:
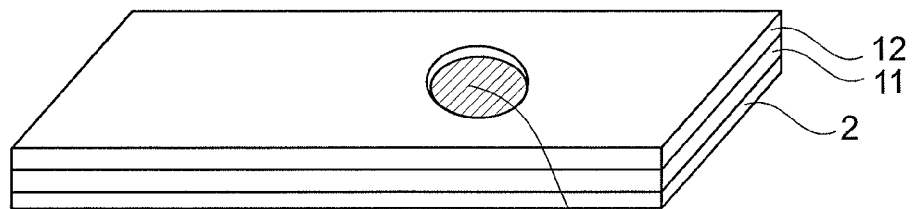
FIG. 4 shows a further embodiment of test strip removed from a stack of test strips.
Figure 5:
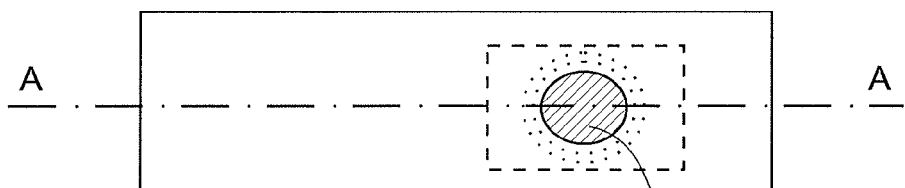
FIG. 5 shows a further view of FIG. 4.
Figure 6:
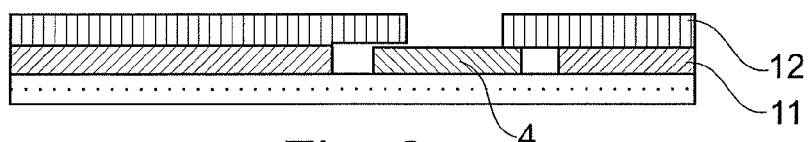
FIG. 6 shows a sectional view of FIG. 5 along a section line A-A.

In the embodiment illustrated in the FIGS. 1 and 2, the test field 4 lies exposed on the carrier material 2. In this manner, the test field 4 forms an embossment on the front side of the test strip 1. The FIGS. 4 to 6 illustrate an embodiment of a test strip 1 wherein such an embossment can be avoided. The test strip 1 illustrated in the FIGS. 4 to 6 has a sandwich-like structure.

In the case of the test strip 1 illustrated in the FIGS. 4 to 6, the carrier material 2 forms a bottom film which carries the test field 4 and a spacer 11. As a spacer 11, a double sided adhesive tape can be used, for example. The spacer 11 carries a cover film 12 which has an opening through which a body fluid sample can be fed to the test field 4. In the embodiment illustrated in the FIGS. 4 to 6, the opening is arranged above the test field 4. However, it is also possible to arrange the opening laterally offset with respect to the test field 4 and to feed a body fluid sample to the test field 4 from the opening through a capillary channel or the like running between the cover film 12 and the bottom film 2.

In the case of the test strip 1 illustrated in the FIGS. 4 to 6, the test field 4 can be configured for electrochemical detection, for example by applying electrodes on the bottom film 2 or the cover film 12. Electrodes, for example, can be imprinted or formed by laser structuring. The test strip 1 illustrated in the FIGS. 4 to 6 can also be configured for photometric detection. For a photometric measurement, the bottom film 2 can be configured to be transparent in the region of the test field 4 or can even be completely transparent. However, a photometric measurement can also be performed from the other side of the test strip 1, for example through the opening in the cover film 12 or, in the case of an opening arranged laterally offset with respect to the test field 4, can be carried out through a cover film 12 which is configured to be transparent at least in the region of the test field 4 or is even completely transparent.

The test strip 1 illustrated in the FIGS. 4 to 6 has a chamber that is formed by the bottom film 2, the spacer 11 and the cover film 12. In the case of a stack 10 of carriers consisting of such test strips 1, this chamber is closed by a test strip 1 adhesively bonded thereon. Thus, the test strips 1 form in each case a closure of the chamber of an adjacent test strip 1.

Figure 7:
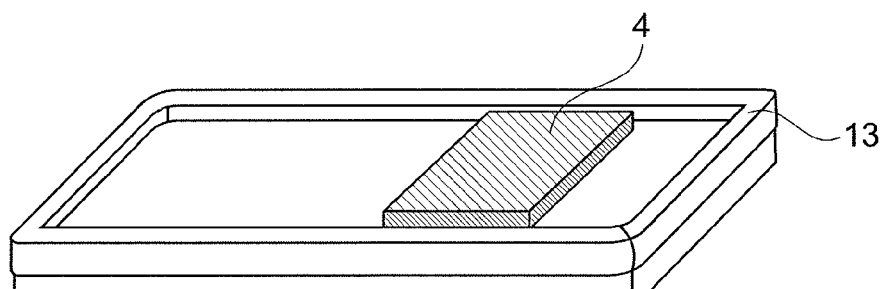
FIG. 7 shows a further embodiment of a test strip removed from a stack of test strips.
Figure 8:
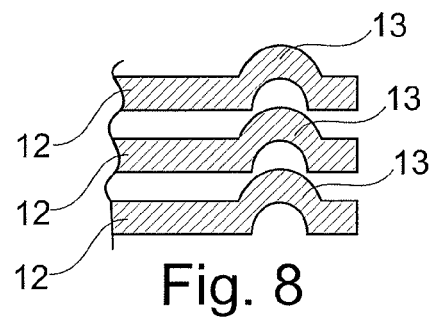
FIG. 8 shows a schematic illustration of a detail of a sectional view of an embodiment of a stack of test strips.

In FIG. 7, another embodiment of a test strip 1 is illustrated. In this embodiment, the test field 4 is surrounded by a circumferential bead 13 which is part of a lateral chamber wall enclosing the test field 4. The bead 13 can be formed by a frame that is glued on, for example. FIG. 8 schematically shows another possibility for forming a bead, namely by means of a circumferential seam.

Although embodiments of the invention have been described using specific terms, such description is for illustrative purposes only, and it is to be understood that changes and variations obvious to the skilled artisan are to be considered within the scope of the claims that follow and their equivalents.

REFERENCE LIST

1 Test strip
2 Carrier material
3 Layer
4 Test field
5 Adhesive
6 Desiccant
7 Adhesive
8 Protective layer
9 Cover strip
10 Stack of test strips
11 Spacer
12 Cover film
13 Bead

What is claimed is:

1. A stack of test strips, comprising a plurality of individual strips which are stacked on top of each other and at least a portion of each of the plurality of test strips carries a test field for examining a body fluid sample, each test field comprising detection reagents, wherein adjacent test strips lying on top of one another are detachably adhesively bonded to each other so that the test strips can be individually removed from the stack, wherein in the stack the test field of each test strip is packed in a sealed chamber having a bottom, an adhesive that surrounds the test field, and a closure that is formed by the adjacent strip.

2. The stack according to claim 1, wherein the chambers contain a desiccant.

3. The stack according to claim 1, wherein the adjacent test strips form the bottom and the ceiling of the chamber lying between them.

4. The stack according to claim 3, wherein the adjacent test strips are adhesively bonded to each other by the adhesive which is arranged between the adjacent test strips and surrounds the test field arranged between the adjacent test strips.

5. The stack according to claim 4, wherein the adhesive forms lateral walls of each of the chambers.

6. The stack according to claim 1, wherein the adhesive adheres differently on a front side than on a back side of each of the test strips so that when removing a selected test strip from the stack, the adhesive disengages always from a same one of the front and back sides of the test strips.

7. The stack according to claim 1, wherein the stack is surrounded at its lateral sides by a protective layer.

8. The stack according to claim 1, wherein the individual test strips are stacked in offset relation on top of the adjacent test strip.

9. The stack according to claim 1, wherein the stack is covered on its lateral sides with an adhesive.

10. The stack according to claim 1, wherein the stack is encased by a film.

11. The stack according to claim 10, wherein the film is a metal film.

12. The stack according to claim 1, wherein at least a portion of the plurality of test strips include front sides having an access to the test field that are roughened to increase the adhesion of an adhesive between the adjacent test strips.

13. The stack according to claim 1, wherein at least a portion of the plurality of the test strips include front sides having an access to the test field that is covered with a material increasing adhesion of an adhesive between the adjacent test strips.

14. The stack according to claim 1, wherein at least a portion of the plurality of the test strips include back sides labeled with human readable characters.

15. The stack according to claim 1, wherein at least a portion of the plurality of the test strips include back sides labeled with machine-readable characters.

16. The stack according to claim 1, wherein the last test field of a stack is closed by an adjacent test strip without a test field.

17. A method for producing a stack of test strips, comprising:

stacking a plurality of individual strips on top of each other, wherein each of test strips includes a front side and an opposite back side and at least a portion of each of the plurality of test strips includes a test field for examining a body fluid sample on the front side thereof, each test field comprising detection reagents, wherein individual test strips which carry the test fields are adhesively bonded to an adjacent test strip to form a stack configured with the front side of the test strips which carry the test fields adhesively bonded to the back side of the adjacent test strip; and stacking of the plurality of individual test strips encloses the test fields in sealed chambers each having a bottom, an adhesive that surrounds the test field, and a closure that is formed by the adjacent strip.

18. The method according to claim 17, wherein for adhesive bonding, the individual strips are placed into a holder which holds the individual test strips spaced apart from each other so that the front side of the test strips which carry the test fields faces toward the back side of the adjacent strip to which it is to be adhesively bonded, and then adhesive is filled into the gaps between the adjacent test strips.

19. A stack of test strips, comprising a plurality of individual test strips which are stacked on top of each other and at least a portion of each of the plurality of test strips carries a test field for examining a body fluid sample, each test field comprising detection reagents, wherein adjacent test strips lying on top of one another are detachably adhesively bonded to each other so that the test strips can be individually removed from the stack, wherein in the stack the test field of each test strip is packed in a sealed chamber having a bottom and a closure that is formed by the adjacent test strip, wherein the adjacent test strips form the bottom and the ceiling of the chamber lying between them, and wherein the adjacent strips are adhesively bonded to each other by an adhesive which is arranged between the adjacent test strips and surrounds the test field arranged between the adjacent test strips.

* * * * *